(12) United States Patent
Liao et al.

(10) Patent No.: US 8,183,041 B2
(45) Date of Patent: May 22, 2012

(54) METHOD OF TISSUE REPAIR USING A MULTI-LAYERED MATRIX

(75) Inventors: Chun-Jan Liao, Taipei (TW); Ching-Chuan Jiang, Taipei (TW); Hong-Sen Chiang, Taipei (TW); Yu-Ru Lin, Ilan (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 346 days.

(21) Appl. No.: 12/385,775

(22) Filed: Apr. 20, 2009

(65) Prior Publication Data

US 2009/0208578 A1  Aug. 20, 2009

Related U.S. Application Data

(62) Division of application No. 11/413,020, filed on Apr. 28, 2006, now abandoned.

(30) Foreign Application Priority Data

Dec. 29, 2005 (TW) ............................... 94147253 A

(51) Int. Cl.
*C13N 5/08* (2006.01)
(52) U.S. Cl. ...................................................... 435/395
(58) Field of Classification Search .................. 435/395
See application file for complete search history.

(56) References Cited

U.S. PATENT DOCUMENTS

| 6,306,169 | B1 | 10/2001 | Lee et al. |
| 2003/0109034 | A1 | 6/2003 | Liao et al. |
| 2004/0078090 | A1 | 4/2004 | Binette et al. |
| 2004/0121459 | A1 | 6/2004 | Liao et al. |
| 2005/0038520 | A1 | 2/2005 | Binette et al. |
| 2005/0170012 | A1 | 8/2005 | Dalal et al. |

FOREIGN PATENT DOCUMENTS

WO  WO-02/070029 A2  9/2002

OTHER PUBLICATIONS

Karp, et al, "Fabrication of Precise Cylindrical Three-Dimensional Tissue Engineering Scaffolds for in Vitro and in Vivo Bone Engineering Applications," J. Craniofac. Surg., 2003, vol. 14, No. 3, pp. 317-323.
Notice of Allowance issued on Jan. 17, 2012 in corresponding U.S. Appl. No. 12/385,781.

*Primary Examiner* — Kevin K. Hill
(74) *Attorney, Agent, or Firm* — Birch, Stewart, Kolasch & Birch, LLP

(57) ABSTRACT

A multi-layered matrix, a method of tissue repair using the same, and multi-layered implant prepared thereof are provided. The multi-layered matrix comprises a first element and a second element connected thereto, and the second element comprises a hollow cavity. The first and the second elements are composed of a composite material comprising a bioabsorbable porous material.

14 Claims, 11 Drawing Sheets (9 of 11 Drawing Sheet(s) Filed in Color)

METHOD OF TISSUE REPAIR USING A MULTI-LAYERED MATRIX

This application is a Divisional of application Ser. No. 11/413,020, filed on Apr. 28, 2006 now abandoned, which claims priority under 35 U.S.C. §119(a) of Patent Application No. 94147253 filed in Taiwan R.O.C. on Dec. 29, 2005, the entire contents of which are hereby incorporated by reference.

BACKGROUND OF THE INVENTION

1. Field of the Invention

The present invention relates to tissue repair, and in particular multi-layered matrix combined with cell blocks for tissue repair.

2. Description of the Related Art

Articular cartilage formed on the articular extremities, or surface of bones is a multi-functional tissue and due to elastic property, can break the force of concussions, lubricate the surface of bones with low friction coefficient, and enable perfect ease and freedom of movement between the bones. Cartilage cells, chondrocytes, are about 2% by weight of the articular cartilage and covered with plenty of extracellular matrices. The major difference of articular cartilage to other tissues is that it does not contain blood-vessels, lymphatic vessels, or nerves. Cartilage metabolism is relatively slow in comparison with other tissues; hence, it is much more difficult for defects in cartilage to heal spontaneously. Patients with articular cartilage defects may not feel pain since no nerve is distributed in the articular cartilage. Chondrocytes covered by cell matrices are well-differentiated cells and have low division ability. In addition, mesenchymal stem cells will not be evoked and migrated to the injured area since cartilage lacks blood vessels and lymphatic vessels.

Articular cartilage defects can be classified into partial thickness defect and full thickness defect according to their severity. Partial-thickness defect is a lesion or erosion on the cartilage tissue of the articular surface that does not reach the subchondral bone whereas full-thickness defect penetrates the subchondral bone. With the advances in surgery and arthroscopy, partial thickness defects may be treated or its symptoms may be relieved by surgery or arthroscopic methods such as abrasion arthroplasty, debridement and lavage, high tibial osteotomy, however, these surgeries cannot treat severe damage such as full thickness defects. As a result, patients are faced with the only choice of undergoing both joint excision and replacement with an artificial joint to relieve the pain and regain joint function. In the United States, it is estimated that over 150,000 knee replacement operations caused by full thickness defects annually and the number of such operations is increasing year by year. Artificial joints are expensive as is replacement operation. In addition, artificial joints made of metal only have a ten- to twenty-year life-span. For young patients, a second replacement operation is inevitable, however, older patients may not be able to receive a second replacement operation and become disabled at the rest of their life. Development of a new treatment for full thickness defects of cartilage is therefore very important.

Methods available to treat cartilage full thickness defects include microfracturing and drilling. This technology is a marrow stimulating arthroscopic procedure to penetrate the subchondral bone to induce fibrin clot formation and the migration of primitive stem cells from the bone marrow into the defective cartilage location. More particularly, the base of the defective area is shaved or scraped to induce bleeding. An arthroscopic awl or pick is then used to make small holes or microfractures in the subchondral bone plate. The end of the awl is manually struck with a mallet to form the holes while care is made not to penetrate too deeply and damage the subchondral plate. The holes penetrate a vascularisation zone and stimulate the formation of a fibrin clot containing pluripotential stem cells. The clot fills the defect and matures into fibrocartilage. Microfracturing the subchondral bone plate can be a successful procedure for producing fibrocartilaginous tissue and repairing defective articular cartilage, however, it still has some disadvantages. For example, the microfractures or holes are manually created. If the holes are not deep enough, then the formation of the fibrin clot may not occur. On the other hand, if the holes are too deep, the subchondral bone plate can be damaged and lead to unwanted consequences and complications. In addition, the fibrocartilage formation may fill the defects, but the cartilage function cannot be totally restored. Another technology is Mosaic Plasty procedure developed by a Hungarian surgeon in 1995. This technique involves using a series of dowel cutting instruments to harvest a plug of articular cartilage and subchondral bone from a donor site, which can then be implanted into a core made into the defect site. By repeating this process, transferring a series of plugs, and by placing them in close proximity to one another, in mosaic-like fashion, a new grafted hyaline cartilage surface can be established. The result is a hyaline-like surface interposed with a fibrocartilage healing response between each graft. The advantages of this technique include the grafts are the patient's own tissue and allograft or xenograft rejection can be prevented. In addition, the grafts are biphasic joint containing cartilage and bone and can be implanted to the articular surface to provide excellent support while the surrounding bone tissue grows into the bone portion of the grafts. This procedure, however, is technically difficult. In addition, the grafts are obtained from the unstressed area of the patient, which is limited to a restrained area. The grafting may also destroy the integrity of the joint.

Recently, a new approach for restoration of articular cartilage defects by ex vivo multiplied autologous cartilage has been developed. Chondrocytes from healthy articular cartilage are harvested and the extracellular matrices are digested by enzymes. Chondrocytes are multiplied outside the body for 11 to 21 days to be more than ten times the original number. The cell concentration is adjusted to $2.6 \times 10^6 - 5 \times 10^6$ cells/ml, and the cells are then injected into the defect site covered with a layer of periosteum by suturing prior to the injection. This technique is under clinical trial, however, and faces a problem in that chondrocytes are dedifferentiated during the ex vivo multiplication step. The originally rounded chondrocytes become spindle-shaped fibrocartilages and the biochemical properties of the cells are also altered. In addition, the steps of obtaining and suturing autologous periosteum cannot be performed under endoscope. Moreover, it requires at least two surgical procedures (i.e., one to harvest the cells and one to reimplant them); it is relatively expensive; and there are limits in the size of lesion, and the number of lesions, that can be treated.

Other techniques combine materials and cells to repair full thickness defects in cartilage or bone. Biomedical materials are selected based on the physical and mechanical properties of cartilage or bone. For cartilage, naturally occurring or synthetic bioabsorbable polymeric materials are selected, such as collagen, gelatin, alginate, poly (glycolide), poly (lactide) (PLLA), poly (glycolide co-lactide) (PLGA). For bone, biomedical ceramic materials are selected, such as hydroxyapatite, tricalcium phosphate, calcium carbonate, or calcium sulfate. The combination of bioabsorbable polymeric materials and biomedical ceramic materials to mimic bones has also been proposed. As for the structure of cartilage, porous structure is prepared to introduce surrounding tissues thereto or as a scaffold for the implanted cells. In addition, the combination of chondrocytes and gel to from a hydrogel with cells has been proposed. The hydrogel with cells can be attached on the bone-layer material to from a biphasic structure of bone and cartilage. The bone-layer material is also porous to introduce surrounding bone tissue thereto since bone tissue has a stronger regeneration ability than cartilage. As for the combination of materials and cells, small amount of autologous cartilage tissue is harvested, digested with enzymes to remove extracellular matrices and release chondrocytes, and the chondrocytes are implanted into a porous scaffold for multiplication. An appropriate amount of multiplied chondrocytes are then implanted to the defect site. In general, this technique is used for simple evenly-distributed tissue, not for multi-layered tissue. When two different cells are implanted in a porous matrix, cells may flow and mix since the cell size is smaller than the pore size of the matrix. The recent technique for multi-layer cultivation involves ex vivo multiplication of cartilage and bone tissues separately, implantation of the multiplied cartilage and bone tissues to two different porous matrices respectively, combination of the two matrices containing cartilage and bone tissues, and fusion of the borders of the two matrices by refusion cultivation to form a biphasic matrix. This technique is, however, time-consuming and also not clinically applied yet.

It therefore would be advantageous to provide a more effective method of tissue repair using a multi-layered matrix.

BRIEF SUMMARY OF THE INVENTION

A detailed description is given in the following embodiments with reference to the accompanying drawings.

Accordingly, the invention provides a multi-layered matrix and a method of tissue repair using the same to solve the drawbacks of the conventional articular cartilage restoration. The multi-layered matrix was designed to have differential structures to grow different cells in different portions of the matrix by the structure of the matrix and the volume differences of tissues. The matrix containing multi-layered tissues can be implanted into the defect site of a subject to repair the defect site with the tissues.

An embodiment of the invention provides a multi-layered matrix. The matrix comprises a first element and a second element connected thereto, and the second element comprises a hollow cavity. The first and the second elements are composed of a composite material comprising a bioabsorbable porous material. The porous material of the first element is for the growth of the surrounding cells of an implanted site in a living subject, and the hollow cavity of the second element is seeded with a cell block prior to the implantation of the living subject.

Also provided is a method of tissue repair using the multi-layered matrix. The method comprises providing the multi-layered matrix, seeding a cell block into the hollow cavity of the multi-layered matrix, and implanting the multi-layered matrix containing the cell block into a defect site of a living subject.

Further provided is a multi-layered implant prepared the method as above described.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The present invention can be more fully understood by reading the subsequent detailed description and examples with references made to the accompanying drawings, wherein:

FIG. 1A is a lateral view and FIG. 1B is a cross-section view.

FIG. 2A shows the porous structure surrounding the hollow cavity, FIG. 2B shows the porous structure beneath the hollow cavity, and FIG. 2C shows the interface between the porous structures surrounding and beneath the hollow cavity.

FIG. 3A shows the minced cartilage, and FIG. 3B shows the cartilage being digested by enzymes for 4 hours after minced.

FIG. 4A is a lateral view, and FIG. 4B is a cross-section view.

FIGS. 5A and 5B shows HE staining, FIG. 5C shows safranin O staining, FIG. 5D shows collagen type II staining, and FIG. 5E shows collagen type I staining.

FIG. 6A shows a defect formed on the knee joint of the Lee-Sung strain miniature pig, FIG. 6B shows a biphasic implant containing chondrocytes implanted into the defect site.

FIG. 8A is the control group, and FIG. 8B is the experimental group.

DETAILED DESCRIPTION OF THE INVENTION

Figure 1A:
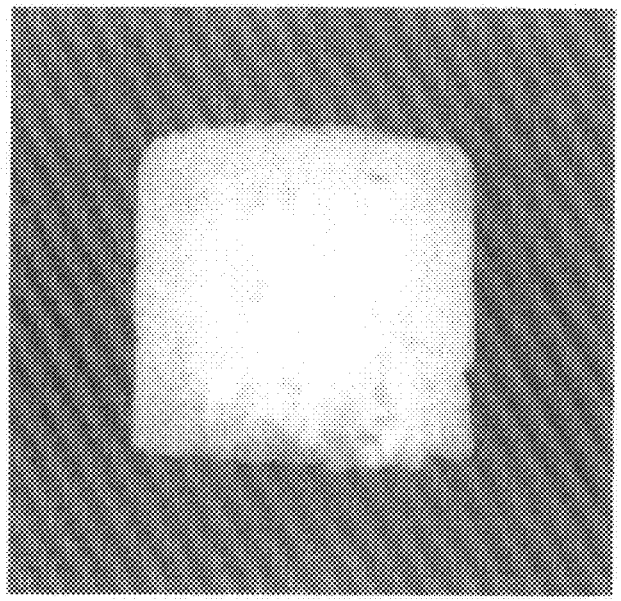
FIGS. 1A and 1B are photographs of the multi-layered matrix of an embodiment of the invention.

The following description is of the best-contemplated mode of carrying out the invention. This description is made for the purpose of illustrating the general principles of the invention and should not be taken in a limiting sense. The scope of the invention is best determined by reference to the appended claims.

A multi-layered matrix, a method of tissue repair using the same, a multi-layered implant prepared thereof are provided.

The multi-layered matrix of the embodiment of the invention is a biphasic matrix which can be implanted into a defect of cartilage and bone tissues. A hollow cavity is on the upper side of the matrix for tissue block containing cells. The size differences of the tissue and the porous structure of the matrix facilitate controlled distribution to centralize the chondrocytes in the upper cavity of the biphasic matrix. The biphasic matrix is then implanted into a defect site of a living subject to reconstruct tissue therein.

The inventors have developed a method and carrier for culturing multi-layered tissue in vitro. The method comprises providing a porous multi-layered carrier having a hollow cavity, placing tissue blocks within the hollow cavity of the porous multi-layered carrier, seeding cells into the carrier, and incubating the tissue blocks and cells within the carrier. With the structure of the carrier and the volume differences between tissue blocks and cells, the tissue blocks and cells can be grown into a two-layered cartilage tissue in vitro for multi-layered tissue repair. The inventors further modified the method and carrier as above described and found that the multi-layered porous matrix containing cells or tissue blocks can be directly implanted into the defect site of a living subject without the ex vivo incubation step. The multi-layered porous matrix containing tissue blocks or cells were then subjected to Mosaic Plasty procedure. A fillister having similar size to the biphasic matrix was created on the defect site of a living subject. An autologous cartilage tissue block was collected from the unstressed area of the articular cartilage. For enhancing the filling area, the cartilage tissue was minced into small pieces and digested by enzymes to release chondrocytes. The partially digested tissue blocks were then placed into the hollow cavity of the biphasic matrix. Tissue blocks were centralized in the upper hollow cavity since the pore size of the porous structure surrounding the hollow cavity is smaller than the tissue blocks. The biphasic implant containing the tissue blocks was then implanted into the fillister on the defect of the articular cartilage to regenerate tissue and repair the articular cartilage defect. Similarly, autologous chondrocytes can be multiplied in vitro, the cell blocks or cells combined with gel or other biomaterials can be placed into the hollow cavity of the biphasic matrix, and the biphasic matrix containing the cells can be implanted into a fillister created on the defect site to repair large defect area.

With the embodiment of the method of tissue repair of the invention, only a small amount of cartilage tissue rather than bone tissue are collected for the implant, avoiding destruction of the integrity and mechanical property of the joint. In addition, the collected tissue blocks are minced and digested with enzyme, enlarging the repair area and enhancing cell propagation and fusion effects. Moreover, this method is an one-step operation which can be manipulated under endoscope to reduce pain and hospitalization time.

Accordingly, an embodiment of the invention provides a multi-layered matrix. The matrix comprises a first element and a second element connected thereto, and the second element comprises a hollow cavity. The first and the second elements are composed of a composite material comprising a bioabsorbable porous material. It is provided that the porous material of the first element is for the growth of the surrounding cells of an implanted site in a living subject, and the hollow cavity of the second element is seeded with a cell block prior to the implantation of the living subject to restore the implant site.

The composite material comprising the bioabsorbable porous material includes, but is not limited to, polylactic acid (PLA), polyglycolic acid (PGA), poly(glycolide co-lactide) (PLGA), polyanhydride, polycapralactone (PCL), polydiester, polyorthoester, collagen, gelatin, hyaluronic acid, chitosan, or polyethylene glycol (PEG), preferably poly(glycolide co-lactide) (PLGA). The pore size of the porous matrix ranges from 50 to 1000 µm. The composite material may further comprise other materials, including, but are not limited to, hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), or calcium pyrophosphate (CPP), preferably tricalcium phosphate (TCP).

The embodiment of the multi-layered matrix, when used for joint defect repair, can be implanted into a joint of a living subject. The cell block can be cartilage. The cartilage can be obtained from the implantation subject or from other living organisms. In addition, the cartilage tissue can be incubated ex vivo. The size of the cell blocks range from 100 to 2,000 µm.

Also provided is a method of tissue repair using the multi-layered matrix. The method comprises providing the multi-layered matrix, seeding a cell block into the hollow cavity of the multi-layered matrix, and implanting the multi-layered matrix containing the cell block into a defect site of a living subject.

The cell block can be a minced tissue block, a tissue and cell aggregate prepared from a tissue block minced and digested with enzymes to release partial cells from the tissue block, or an in vitro multiplied cell block combined with gel. The enzyme digestion time ranges from 5 min to 24 hours. The enzymes include, but are not limited to, collagenase, hyaluronidase, trypsin, or proteinase. When the defect site is located on a joint, the cell block can be cartilage and the enzyme can be collagenase.

The cell block can be a cell aggregate from in vitro cultivation of a cell. When the implant site is a joint defect, a chondrocyte can be in vitro cultured to form the cell aggregate.

Moreover, the cell block can be a granular carrier attached with cells if necessary.

It is to be noted, the size of the cell block is larger than the pore size of the porous material. For example, the size of the cell block ranges from 100 to 2,000 µm.

Further provided is a multi-layered implant prepared by the method described above.

Practical examples are described herein.

EXAMPLES

Example 1

Preparation of Porous Matrix

The biodegradable polymer used herein was poly (glycolide co-lactide) (PLGA) prepared by ring-open polymerization with a molecular weight of 580,000 determined by gel permeation chromatography. PLGA was mixed with a biomedical ceramic powder, tricalcium phosphate (TCP). Sodium chloride particle with diameter 250 µm was also added to produce apertures. The organic solvent for dissolving polymeric particles was acetone.

Two grams of PLGA was dissolved in 40 ml of acetone. Eight gram of sodium chloride was then added to the solution with a ratio of PLGA/NaCl:20/80% by weight. The mixture was poured into a Teflon mold with a size of 10 cm×10 cm×0.5 cm and then placed in a laminar flow to evaporate the organic solvent. PLGA film containing NaCl particles and having a thickness of 0.8 mm was obtained and trimmed into round slices with a diameter of 8.5 mm and strips with a size of 27 mm×3 mm.

PLGA blocks were evenly dissolved in acetone. Tricalcium phosphate (TCP) was then added to the solution with a ratio of PLGA/TCP:50/50% by weight. The sticky mixture was poured into a Teflon mold and then placed in a laminar flow to evaporate the organic solvent. The block-shaped PLGA/TCP composite material was pulverized in a pulverizer and filtrated with a sieve of 40 to 60 meshes to obtain a polymer particle with a diameter ranging from 250 to 440 µm. The PLGA/TCP composite particles were dry mixed with NaCl particles in a weight ratio of 20/80%.

The above round slice of NaCl particles-contained PLGA was placed in a round-shaped teflon filtering flask having a diameter of 8.5 mm with the lower end thereof connected to an exhaust device. The PLGA strip was surrounded the periphery of the round slice in the Teflon filtering flask to form a round fillister. 0.05 g of NaCl particles were filled into the fillister and tightly flattened. 0.5 g of the mixture of PLGA/TCP composite particles and NaCl particles were then filled the rest space and tightly flattened. The Teflon mold was poured with acetone to immerse the mixture of particles. A negative pressure was exerted by turning on the exhaust valve to draw out superfluous solvent. This step enables the partially dissolved polymer particles to adhere to one another. When an integral structure was formed, a large amount of deionized water was poured onto the top of the filter and the exhaust valve was turned on again to pass the large amount of water through the materials to dialyze and solidify the polymer particles. At the same time, NaCl particles in the interior were washed out by water. The solidified matrix was obtained from the filter and immersed and stirred in a large beaker containing deionized water in which the deionized water was changed every six hours under room temperature for one day to wash out the remaining solvent and salt particles. The solidified matrix was then heat dried in a vacuum oven at 50° C. for one day and a multi-layered porous matrix having an upper hollow cavity was obtained. The multi-layered porous matrix was immersed in 75% alcohol for 6 hours and then in a substantial amount of sterilized phosphate buffered saline (PBS) to replace the alcohol.

Figure 1B:
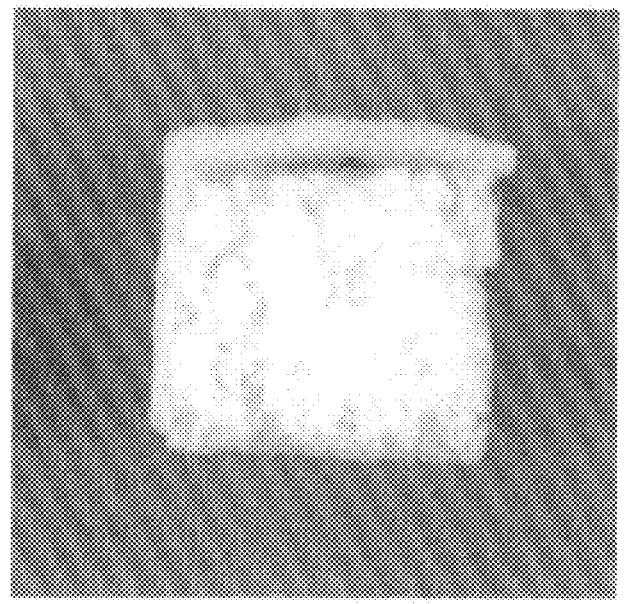
Figure 2A:
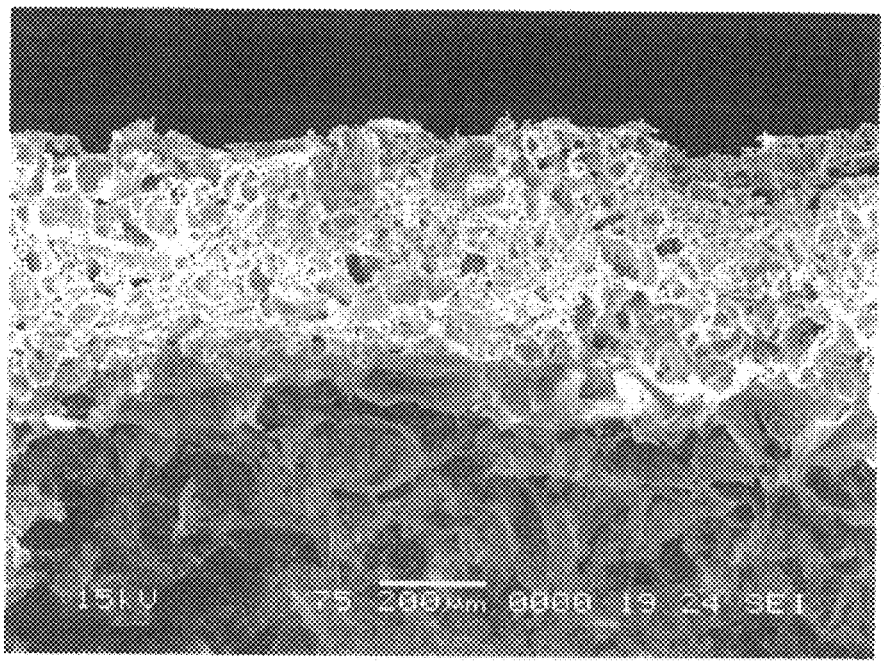
FIGS. 2A~2C are electron microscopic photographs of the multi-layered matrix of the embodiment of the invention.
Figure 2B:
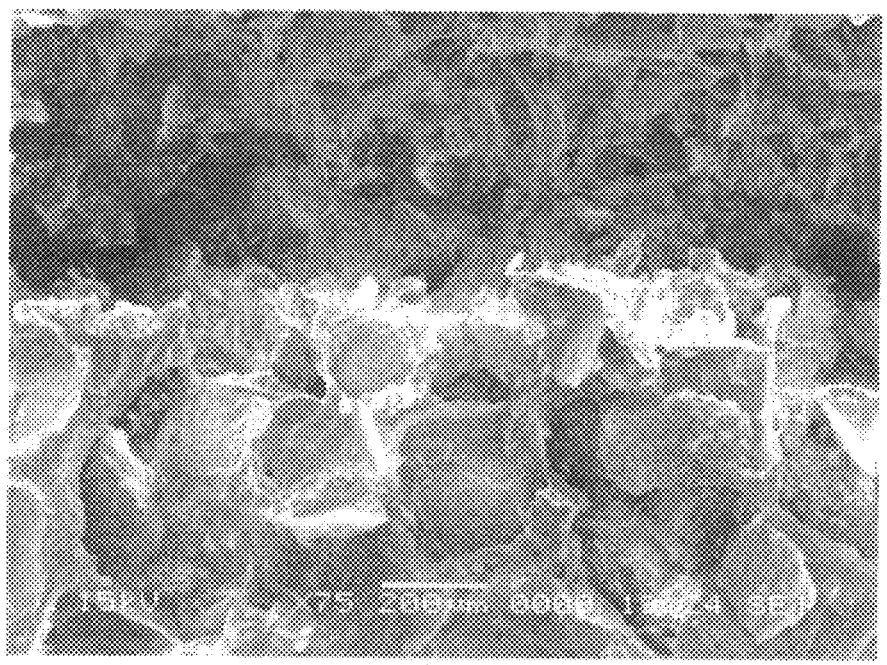
Figure 2C:
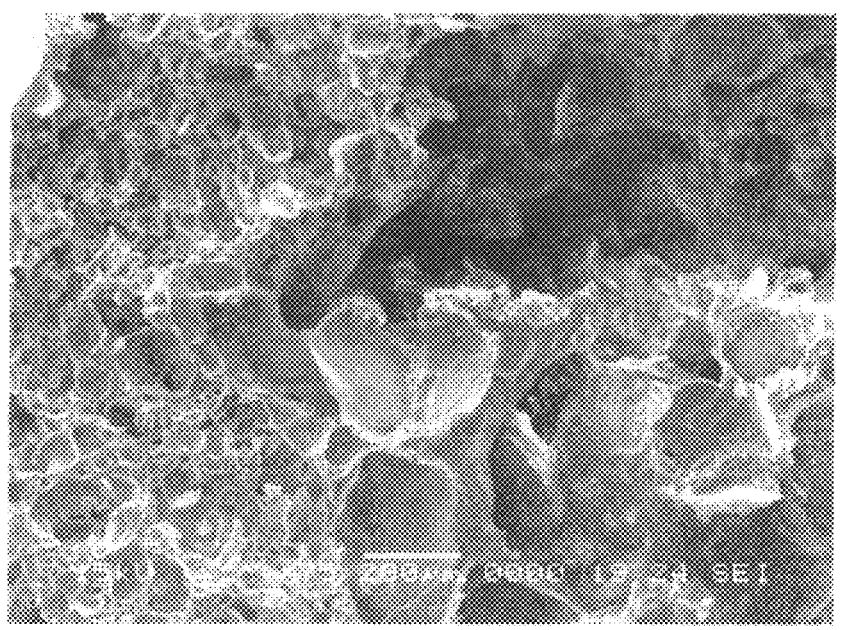

The prepared multi-layered porous matrix is shown in FIGS. 1A and 2B. FIG. 1A is a lateral view and FIG. 1B is a cross section of the prepared multi-layered porous matrix. FIGS. 1A and 1B show a two-layered structure with an upper hollow cavity surrounded by a thick wall and a lower evenly porous structure. The multi-layered porous matrix was also observed under electron microscope and the results were shown in FIG. 2A~2C. FIG. 2A shows the porous structure surrounding the hollow cavity with the pore size and the porosity of 112±41 µm and 84.2±2.4 vol % respectively, FIG. 2B shows the porous structure beneath the hollow cavity with the pore size and the porosity of 115±57 µm and 86.6±3.1 vol % respectively, and FIG. 2C shows the interface between the porous structures surrounding and beneath the hollow cavity. The porous structure of the interface is interconnected and no closed interface was observed.

Example 2

Isolation of Cartilage Tissue and Enzyme Treatment

Figure 3A:
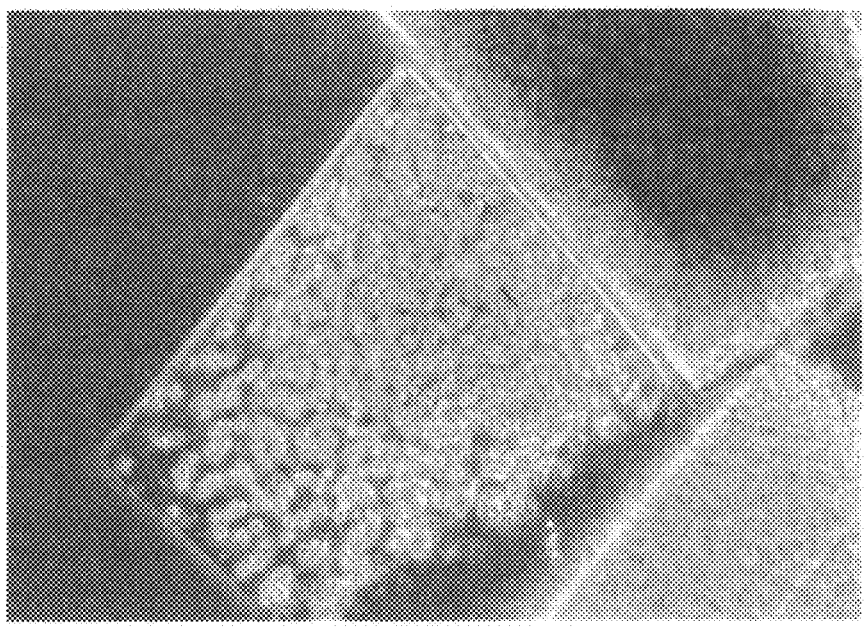
FIGS. 3A and 3B are microscopic photographs of articular cartilage.
Figure 3B:
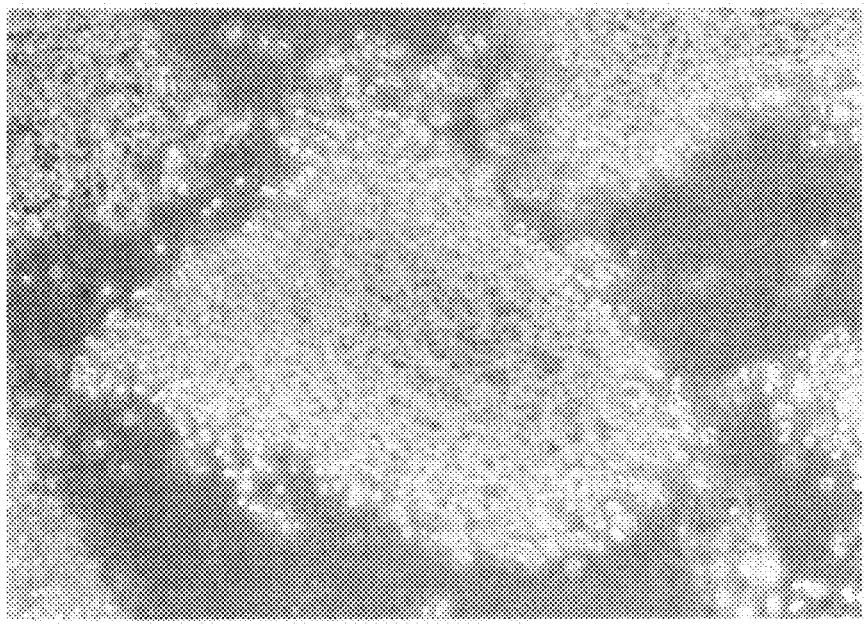

Eight Lee-Sung strain adult (about 12-month-old) miniature pigs with weight of 50~65 kg each were used (half male/half female). The pigs were anesthetized with Pentothal (powder, 2.5 g/ampoule, Abbott, diluted with normal Saline to 100 ml/ampoule) by I.V. injection (marginal ear vein). The surgical site was shaved and sterilized with alcoholic povidine iodine. A vertical incision was made on the midline of the knee joint and extends inside to expose the knee joint. Autologous cartilage was collected with a curette from the unstressed site of the joint until the subchondral bone was exposed. The collected autologous cartilage was placed in a 10-cm petri dish and minced with a scalpel. The minced cartilage tissues were filtrated with a sieve of 20-40 meshes to be in a size ranging 560-800 µm, as shown in FIG. 3A. The filtrated cartilage tissues were placed in a 15-ml centrifugation tube and treated with 5 ml of collagenase (2 mg/ml PBS) at 37° C. for 4 hours to partially release the chondrocytes, as shown in FIG. 3B. The dissolved cartilage tissues were centrifuged at 1500 r.p.m. for 5 minutes to separate the chondrocytes and collagenase. Supernatant containing collagenase was discarded and the remaining cartilage tissues were washed with PBS twice and centrifuged twice to totally remove the collagenase.

Example 3

In Vivo Implantation of the Multi-Layered Matrix Containing the Cartilage Tissue The enzyme treated cartilage tissues were injected into the hollow cavity of the multi-layered porous matrix by an 18-gauge syringe. The tissue blocks may centralize in the upper cavity since they are larger than the pore size of the matrix. A biphasic matrix with the upper cavity containing cartilage tissues and chondrocytes and the lower porous matrix were formed.

3-1: Implantation of Nude Mice

Figure 4A:
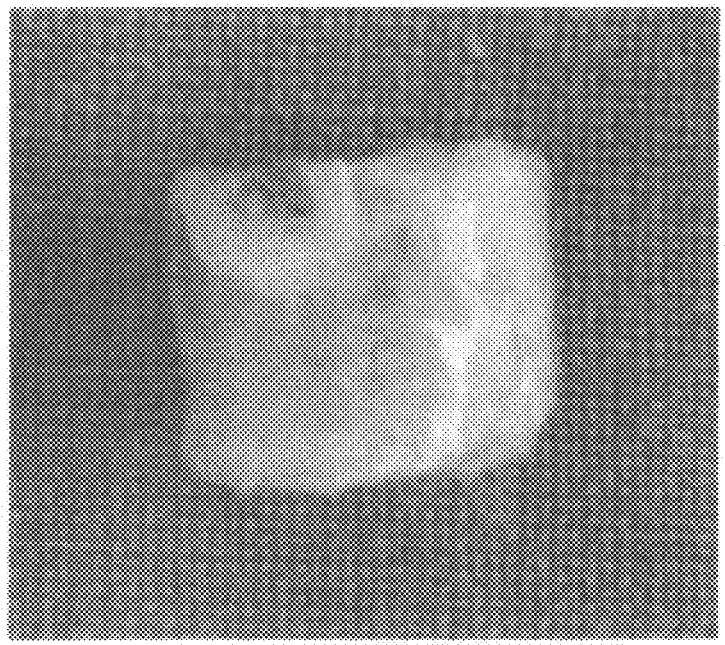
FIGS. 4A and 4B are photographs showing the multi-layered matrix of the embodiment of the invention being seeded with the digested cartilage, implanted into the back of a nude mouse, and retrieved from the mouse after one month.
Figure 4B:
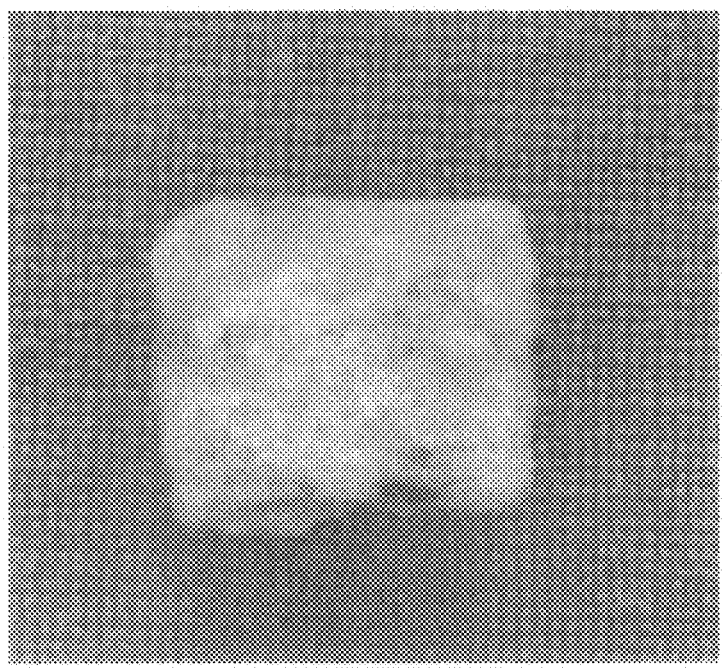
Figure 5A:
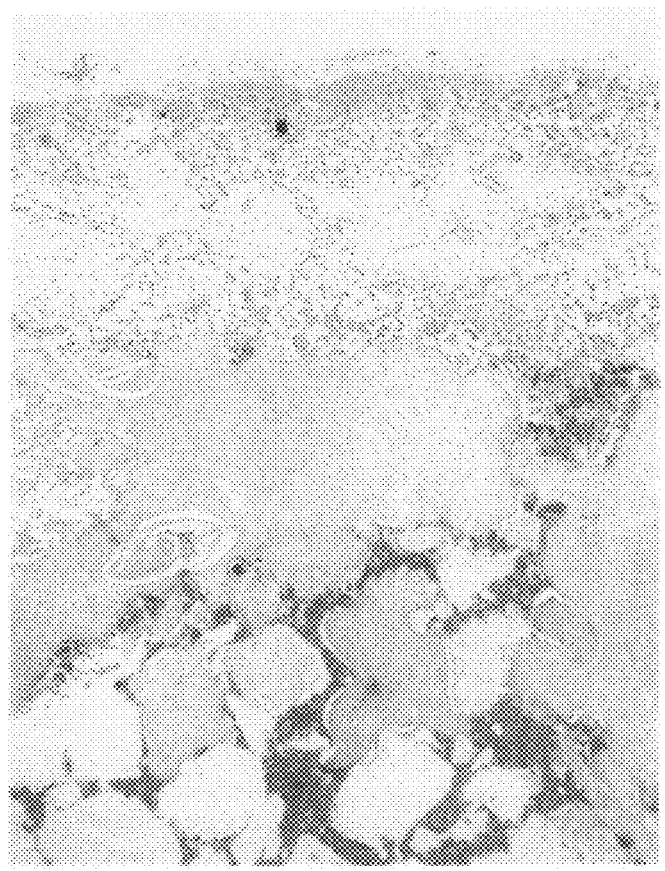
FIGS. 5A~5E are histological photographs showing the multi-layered matrix of the embodiment of the invention being seeded with the digested cartilage, implanted into the back of a nude mouse, and retrieved from the mouse after 1 month.
Figure 5B:
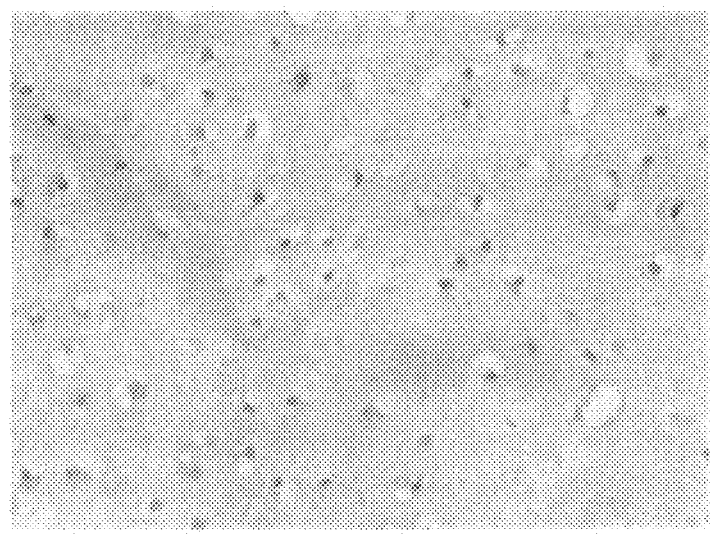
Figure 5C:
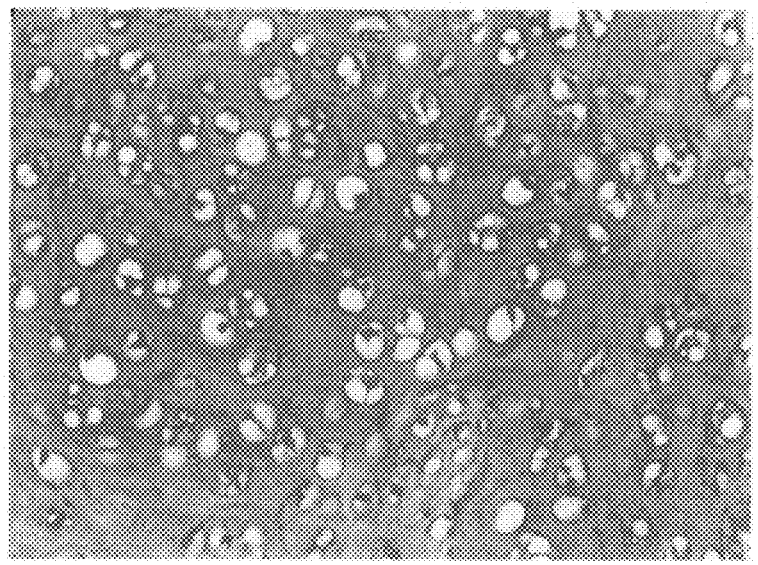
Figure 5D:
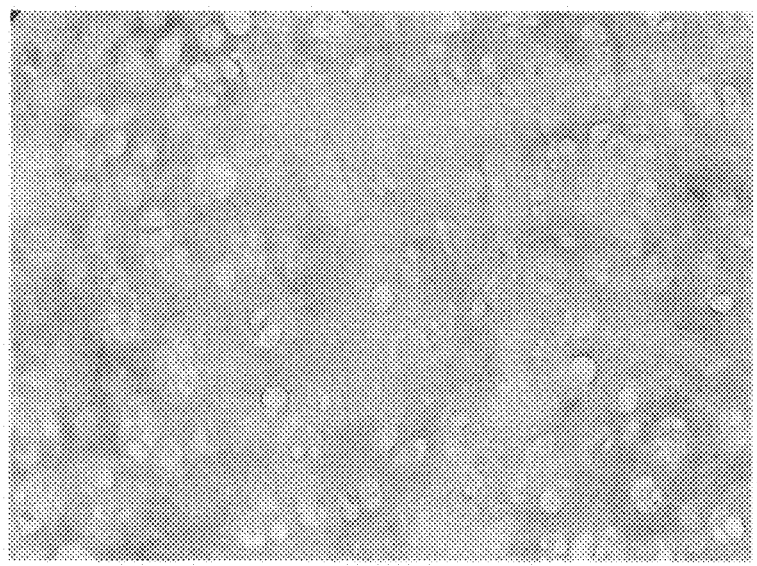
Figure 5E:
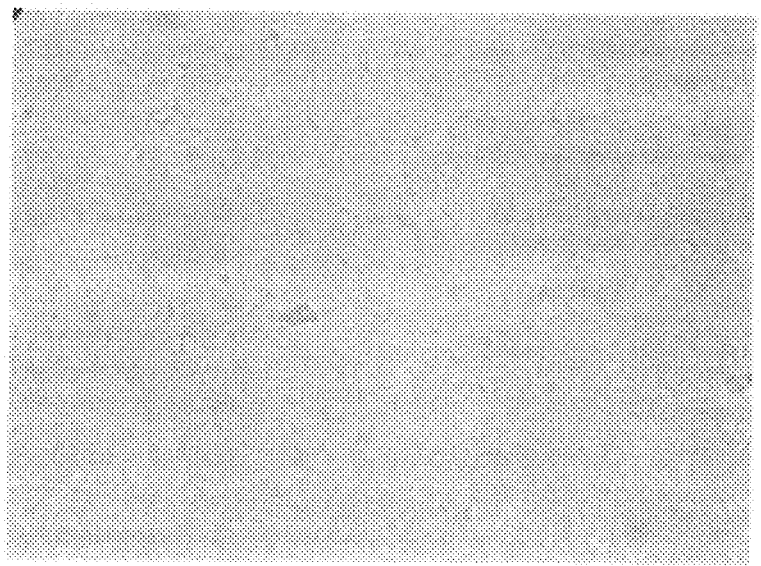

To determine whether the implant containing the cartilage tissues forms two layers of cartilage and bone in vivo, the biphasic matrix was implanted into the back of nude mice and the histological morphology was observed. The operation is as described below. The back of a nude mouse was locally anesthetized and sterilized. An incision with a size of 0.5-1 cm was made subcutaneously, and the biphasic matrix containing the cartilage tissues was implanted into the subcutaneous site of the back of the nude mouse. The incision was then sutured. The nude mouse was raised in its own cage. After 4 weeks, the implant was taken out from the nude mouse and analyzed. The matrix, as shown in FIGS. 4A and 4B, is intact and a new cartilage tissue is grown at the site of the hollow cavity. The histological results are shown in FIG. 5A~5E. FIGS. 5A and 5B are HE staining and the results reveal a newly formed cartilage tissue layer at the site of the hollow cavity extended toward the lower porous structure to form an interface between cartilage and bone. Under a magnified field, as shown in FIG. 5B, the implanted cartilage tissues were apparently fused and the tissue blocks did not have a clear interface. FIGS. 5C and 5D are safranin-O and type II collagen staining respectively, and FIG. 5E is type I collagen staining. The results show apparent safranin-O and type II collagen stain with no type I collagen stain, indicating that the cartilage tissue at the hollow cavity secrets hyaline cartilage specific substance such as type II collagen and does not dedifferentiate into fibrocartilages.

3-2: Implantation of Pig

Figure 6A:
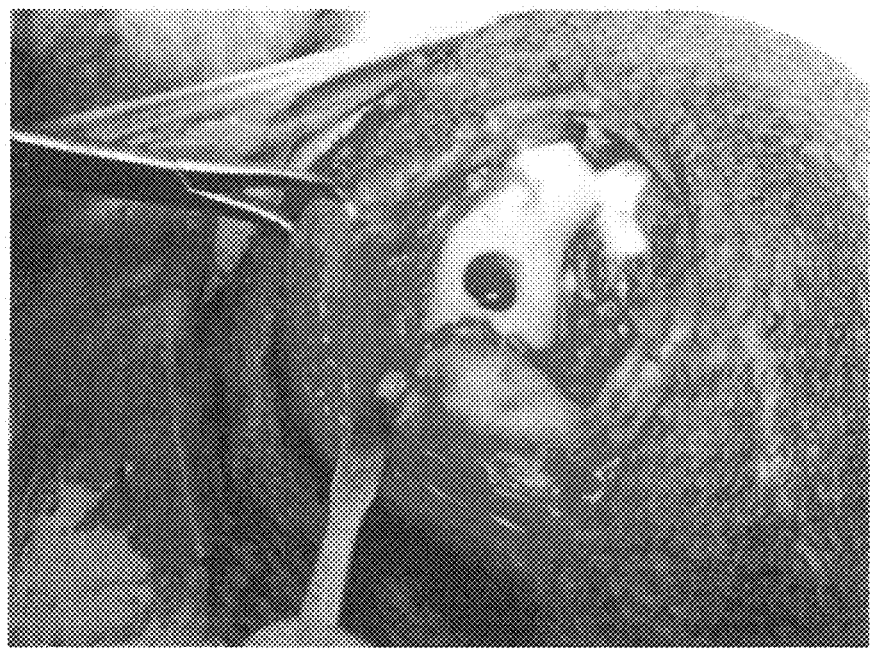
FIGS. 6A and 6B are photographs showing the surgical procedure for implantation of a biphasic implant containing chondrocytes into the knee joint of a Lee-Sung strain miniature pig.
Figure 6B:
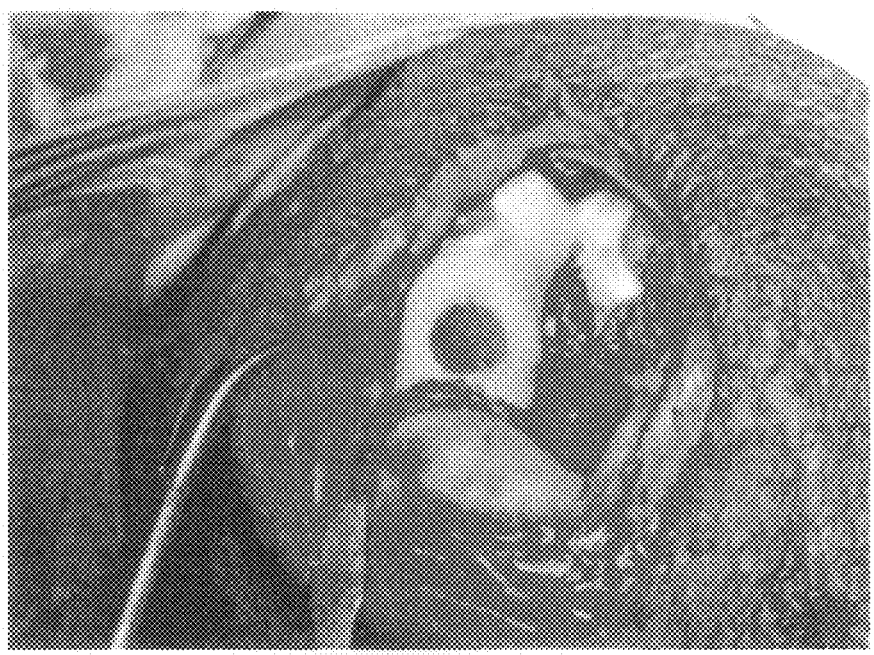
Figure 7:
FIG. 7 is a photograph showing two biphasic implants obtained from the Lee-Sung strain miniature pig after a half-year implantation. The left side is the control group and the right side is the experimental group.
Figure 8A:
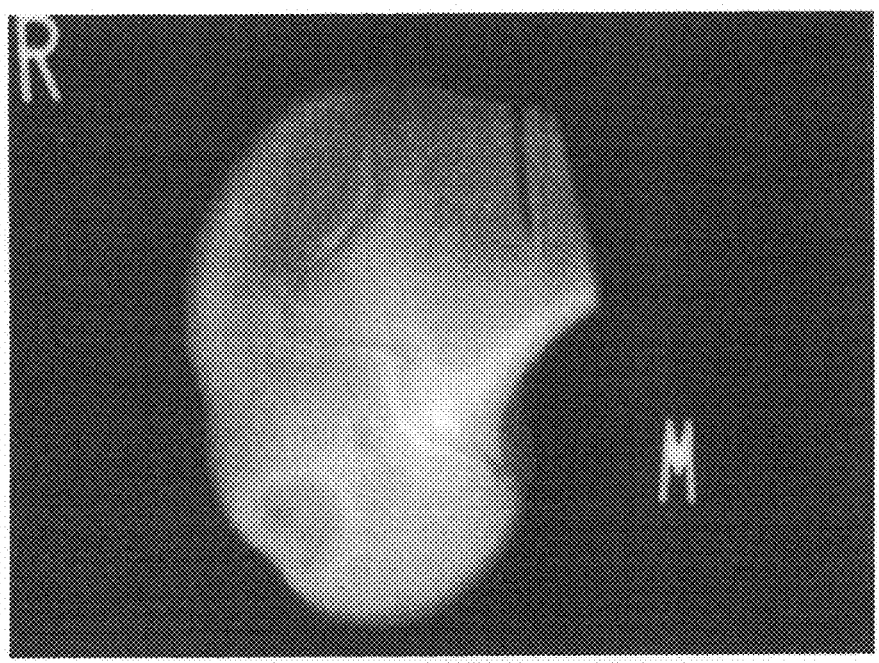
FIGS. 8A and 8B are X-ray results showing the joint after the implantation of the biphasic implant of the embodiment of the invention for half year.
Figure 8B:
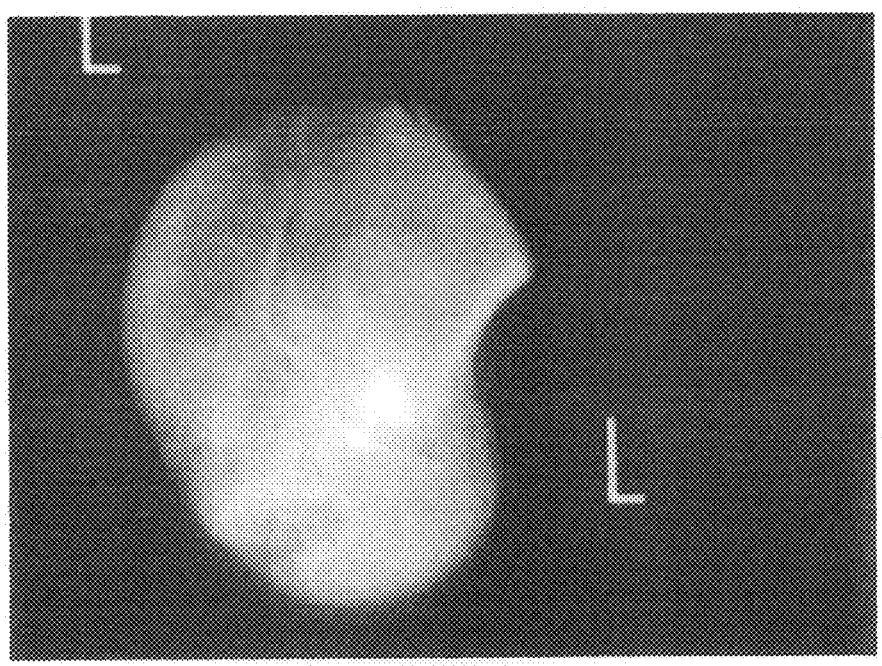

The mid-portion of the distal articular surface of the lateral and medial condylus of femur of a Lee-Sung strain miniature pig was drilled to form a cylindrical hole with a diameter and depth of 8.5 mm. The cartilage and bone tissues including the whole layer of cartilage tissue with a thickness of 2 mm, the subchondral bone, and partial sponge bone in the cylindrical pore were removed, as shown in FIG. 6A. The control group was implanted with a matrix with no tissue, and the experimental group was implanted with the above biphasic matrix with the enzyme-treated autologous cartilage tissues. The implant should fit the cylindrical hole and would not drop out from the hole due to the press-fitting. The articular surface and the implant surface should be at the same level, to avoid step-off, as shown in FIG. 6B. The joint was lavaged and sutured layer by layer. After the surgery, the pig was allowed to stand with four legs. Six months later, the knee joints of the control and experimental groups were observed and the results, as shown in FIG. 7, reveal that the control group (left side) has some regeneration around the defect but could not be completely repaired. The right side is the experimental group and it shows that the defect site is covered with a layer of new cartilage tissues. The joints were observed under X-ray photography as shown in FIGS. 8A and 8B. FIG. 8A shows that the control group has no bone tissue extended into the implant, and FIG. 8B shows that the experimental group has apparent new bone tissue extended into the implant.

By the results given above, the biphasic implant prepared by the embodiment of the method of the invention effectively formed a new cartilage layer at the hollow cavity of the matrix containing cartilage tissues. From the implantation of the animal model of full thickness defect, it shows that the implant of the embodiment of the invention effectively repair full thickness defects.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of repairing tissue comprising the steps of:
   i) providing a multi-layered matrix comprising a first element and a second element connected thereto comprising a hollow cavity, wherein the first and the second elements are composed of a composite material comprising a bioabsorbable porous material;
   ii) seeding a cell block into the hollow cavity of the second element of the multi-layered matrix, wherein the cell block is enzyme-treated for 4 hours before being seeded into the hollow cavity; and
   iii) directly implanting the multi-layered matrix containing the cell block into a defect site of a living subject without an ex vivo incubation of the multi-layered matrix containing the cell block.

2. The method as claimed in claim 1, wherein the bioabsorbable porous material comprises polylactic acid (PLA), polyglycolic acid (PGA), poly (glycolide co- lactide) (PLGA), polyanhydride, polycaprolactone (PCL), polydiester, polyorthoester, collagen, gelatin, hyaluronic acid, chitosan, or polyethylene glycol (PEG), or a mixture thereof.

3. The method as claimed in claim 1, wherein the composite material further comprises a second material, wherein the second material comprises hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), or calcium pyrophosphate (CPP), or a mixture thereof.

4. The method as claimed in claim 1, wherein the porous material has a pore size ranging 50 to 1,000 μm.

5. The method as claimed in claim 1, wherein the cell block is a minced tissue block.

6. The method as claimed in claim 1, wherein the cell block is a tissue block which is minced and enzyme-treated to release partial cells.

7. The method as claimed in claim 1, wherein the enzyme is collagenase, hyaluronidase, trypsin, or proteinase, or a mixture thereof.

8. The method as claimed in claim 1, wherein the defect site is a joint.

9. The method as claimed in claim 8, wherein the cell block is a cartilage tissue.

10. The method as claimed in claim 9, wherein the enzyme is collagenase.

11. The method as claimed in claim 1, wherein the cell block is a cell aggregate.

12. The method as claimed in claim 1, wherein the cell block is a granular carrier attached with a cell.

13. The method as claimed in claim 1, wherein the size of the cell block is larger than the pore size of the porous material.

14. The method as claimed in claim 1, wherein the cell block has a size ranging 100 to 2,000 μm.

* * * * *